(12) United States Patent  (10) Patent No.: US 8,822,383 B2
Sasaki et al.  (45) Date of Patent: Sep. 2, 2014

(54) GERMINATION-STIMULANT CARBAMATE DERIVATIVES AND PROCESS FOR PREPARATION THEREOF

(75) Inventors: Mitsuru Sasaki, Nishinomiya (JP); Yukihiro Sugimoto, Takarazuka (JP); Hirosato Takikawa, Kobe (JP); Hideyoshi Miyake, Nishinomiya (JP); Noritada Matsuo, Amagasaki (JP)

(73) Assignees: National University Corporation KOBE UNIVERSITY, Kobe-shi (JP); Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/638,508

(22) PCT Filed: Mar. 30, 2011

(86) PCT No.: PCT/JP2011/057973
§ 371 (c)(1),
(2), (4) Date: Dec. 4, 2012

(87) PCT Pub. No.: WO2011/125714
PCT Pub. Date: Oct. 13, 2011

(65) Prior Publication Data
US 2013/0085068 A1  Apr. 4, 2013

(30) Foreign Application Priority Data
Mar. 31, 2010 (JP) ................................. 2010-082370

(51) Int. Cl.
A01N 43/08 (2006.01)
A01N 47/18 (2006.01)
A01N 47/20 (2006.01)
C07D 307/60 (2006.01)
C07D 307/64 (2006.01)

(52) U.S. Cl.
CPC ............ C07D 307/60 (2013.01); *C07D 307/64* (2013.01); *A01N 43/08* (2013.01); *A01N 47/18* (2013.01); *A01N 47/20* (2013.01)
USPC ........................................ 504/299; 549/318

(58) Field of Classification Search
CPC .... C07D 307/60; C07D 307/64; A01N 43/08; A01N 47/18; A01N 47/20
USPC ........................................ 504/299; 549/318
See application file for complete search history.

(56) References Cited

U.S. PATENT DOCUMENTS 2,814,627 A * 11/1957 Wheeler et al. ............... 549/304
3,965,119 A   6/1976 Amann et al.

FOREIGN PATENT DOCUMENTS

JP     50-53361 A    5/1975
JP    2006-282513 A  10/2006

OTHER PUBLICATIONS

Cook et al., "Germination of Witchweed (*Striga lutea* Lour.): Isolation and Properties of a Potent Stimulant," Science, vol. 154, pp. 1189-1190, Dec. 2, 1966.
International Preliminary Report on Patentability for International Patent Application No. PCT/JP2011/057973, dated Nov. 13, 2012.
International Search Report issued for International Patent Application No. PCT/JP2011/057973, dated May 31, 2011.
Kondo et al., "Synthesis and Seed Germination Stimulating Activity of Some Imino Analogs of Strigolactones," Biosci. Biotechnol. Biochem., vol. 71, No. 11, pp. 2781-2786, Nov. 7, 2007.
Mangnus et al., "Tentative Molecular Mechanism for Germination Stimulation of *Striga* and *Orobanche* Seeds by Strigol and Its Synthetic Analogues," J. Agric. Food Chem., vol. 40, No. 6, pp. 1065-1070, 1992.
Nefkens et al., "Synthesis of a Phthaloyiglycine-Derived Strigol Analogue and Its Germination Stimulatory Activity toward Seeds of the Parasitic Weeds *Striga hermonthica* and *Orobanche crenata*," J. Agric. Food Chem., vol. 45, No. 6, pp. 2273-2277, 1997.
Sugimoto et al., "Synthesis of All Eight Stereoisomers of the Germination Stimulant Sorgolactone," J. Org. Chem., vol. 63, No. 4, pp. 1259-1267, Feb. 4, 1998.
Sugimoto; Yukihiro, "Chemical and biological studies on interactions between root parasitic weeds and their host plants," Regulation of Plant Growth & Development, vol. 44, No. 1, pp. 2-9, 2009.
Yoneyama et al., "Chemical stimulation of seed germination of root parasitic weeds, *Striga* and *Orobanche* spp.," Chemical Regultaions of Plants, vol. 34, No. 2, pp 181-190, 1999.

* cited by examiner

*Primary Examiner* — Noble Jarrell
*Assistant Examiner* — Valerie Rodriguez-Garcia
(74) *Attorney, Agent, or Firm* — Birch, Stewart, Kolasch & Birch, LLP

(57) ABSTRACT

Provided is a novel compound which can germinate seeds of root parasitic plants, more specifically, a compound represented by the formula:

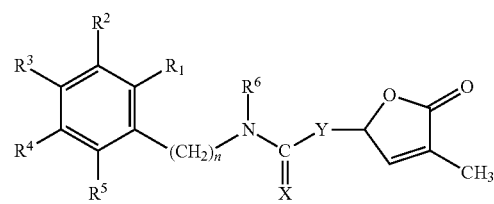

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring,
$R^6$ represents a hydrogen atom or a lower alkyl group,
X and Y are the same or different and each represents an oxygen atom and a sulfur atom, and
n represents an integer of 0, 1 or 2, and a method for controlling root parasitic plants.

14 Claims, No Drawings

GERMINATION-STIMULANT CARBAMATE DERIVATIVES AND PROCESS FOR PREPARATION THEREOF

TECHNICAL FIELD

The present application is filed claiming the priority of the Japanese Patent Application No. 2010-082370, the entire contents of which are herein incorporated by reference.

The present invention relates to a novel carbamate derivative, a process for the preparation thereof, and an agent for controlling a root parasitic plant comprising said compound as an active ingredient.

BACKGROUND ART

*Striga* and *Orobanche* are root parasitic plants, which grow on agricultural crops such as leguminous crops and cereals as a host. *Striga* is distributed in semiarid regions of tropical and subtropical zones of Africa and South Asia, and grow on main agricultural crops such as sorghum and corn as a host. *Orobanche* is widely distributed in Mediterranean and Middle East regions centered on temperate and subarctic zones, and grow on leguminous crops and the like as a host. Root parasitic plants are parasitic in the roots of agricultural crops, and rob nutrients and water from the agricultural crops. As the result, the growth of the agricultural crops is inhibited. Accordingly, root parasitic plants cause great damage to agriculture, and such damage has recently spread to Europe and Australia.

In order to avoid being parasitic in the roots of agricultural crops, it is needed to kill seeds of root parasitic plants in field soil before the cultivation of agricultural crops in the field.

It is known that seeds of root parasitic plants are germinated in the vicinity of a host, and they are not survived in several days after the germination of seeds when they could not be parasitic in the roots of a host. Therefore, if the germination of seeds of root parasitic plants can be induced in agricultural lands before seeding of agricultural crops, i.e., in the absence of agricultural crops, the germinated seeds of root parasitic plants can be killed, and thus the growth inhibition of agricultural crops by root parasitic plants can be controlled.

Heretofore, some compounds capable of inducing the germination of seeds of root parasitic plants have been reported (cf. Non-Patent Literatures 1 and 2).

CITATION LIST

Non-Patent Literature

Non-Patent Literature 1: C. E. Cook, L. P. Whichard, B. Turner, M. E. Wall, G. H. Egley, Science, 1966, 154, 1189-1190

Non-Patent Literature 2: Y. Sugimoto, S. C. M. Wigchert, J. W. J. F. Thuring, B. Zwanenburg, Journal of Organic Chemistry, 1998, 63, 1259-1267

SUMMARY OF INVENTION

Technical Problem

An object of the present invention is to provide a novel compound capable of germinating seeds of root parasitic plants.

Solution to Problem

The present inventors have intensively studied aiming at novel compounds capable of inducing the germination of seeds of root parasitic plants and finally found that the following carbamate derivatives are effective to germinate seeds of root parasitic plants. Thus, the present invention has been completed.

Namely, the present invention relates to the followings:

Namely, the present invention includes the followings:

[1] A compound represented by the formula (1):

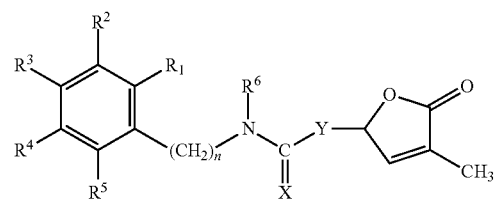

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, X and Y are the same or different and each represents an oxygen atom and a sulfur atom, and n represents an integer of 0, 1 or 2

(hereinafter referred to as "the compound of the present invention);

[2] The compound according to the above [1], wherein $R^1$, $R^2 R^3$, $R^4$, and $R^5$ are the same or different and each represents a hydrogen atom or a lower alkyl group, or $R^2$ and $R^3$ are linked together to form a lower alkylenedioxy group;

[3] The compound according to the above [1], wherein $R^1$ is a hydrogen atom or a lower alkyl group, $R^2$ is a hydrogen atom or a lower alkyl group, $R^3$ is a hydrogen atom or a lower alkyl group, or $R^2$ and $R^3$ are linked together to form a lower alkylenedioxy group, $R^4$ is a hydrogen atom, and $R^5$ is a hydrogen atom;

[4] The compound according to the above [2], wherein $R^1$, $R^2$, $R^3$, $R^4$, and $R^5$ are the same or different and each represents a hydrogen atom or a methyl group, or $R^2$ and $R^3$ are linked together to form a methylenedioxy group, and $R^6$ is a hydrogen atom or a methyl group;

[5] The compound according to the above [1], wherein $R^1$, $R^2$, $R^3$, $R^4$, and $R^5$ is a hydrogen atom;

[6] The compound according to the above [5], wherein $R^6$ is a hydrogen atom or a methyl group;

[7] The compound according to any of the above [1]-[6], wherein X and Y are oxygen atoms;

[8] The compound according to the above [1], which is 4-methyl-5-oxo-2,5-dihydrofuran-2-yl benzylcarbamate, 4-methyl-5-oxo-2,5-dihydrofuran-2-yl phenethylcarbamate, 4-methyl-5-oxo-2,5-dihydrofuran-2-yl methyl(phenyl)carbamate, or 4-methyl-5-oxo-2,5-dihydrofuran-2-yl benzyl(methyl)carbamate;

[9] A process for producing a compound represented by the formula:

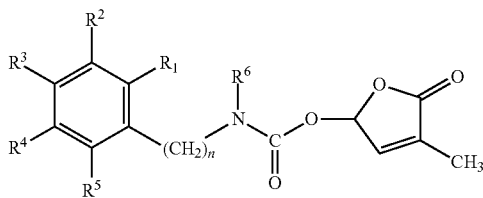

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring,
$R^6$ represents a hydrogen atom or a lower alkyl group, and
n represents an integer of 0, 1 or 2, which comprises reacting a compound represented by the formula:

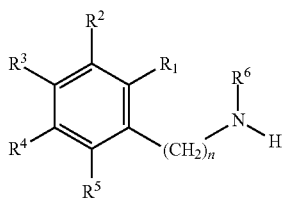

wherein $R^1$, $R^2$, $R^3$, $R^4$, $R^5$, $R^6$ and n are as defined above, with a compound represented by the formula:

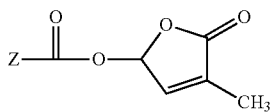

wherein Z represents a halogen atom, in the presence of a base;

[10] A process for producing a compound represented by the formula:

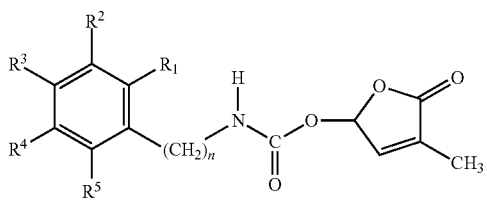

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, and n represents an integer of 0, 1 or 2, which comprises reacting a compound represented by the formula:

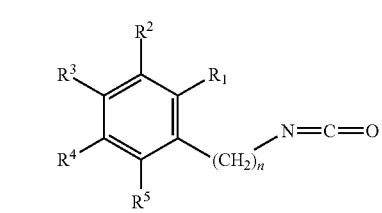

wherein $R^1$, $R^2$, $R^3$, $R^4$, $R^5$ and n are as defined above, with a compound represented by the formula:

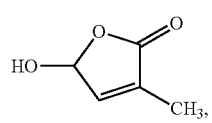

in the presence of a base;

[11] A process for producing a compound represented by the formula:

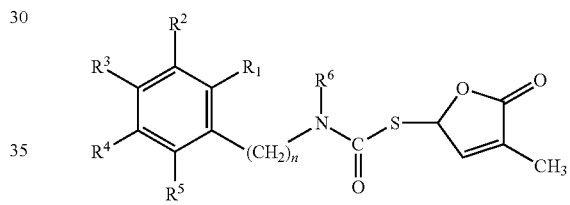

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and
n represents an integer of 0, 1 or 2, which comprises reacting a compound represented by the formula:

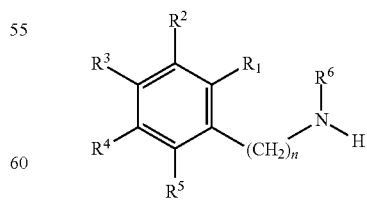

wherein $R^1$, $R^2$, $R^3$, $R^4$, $R^5$, $R^6$ and n are as defined above, with carbon disulfide in the presence of a base, and then reacting the resulting compound with a compound represented by the formula:

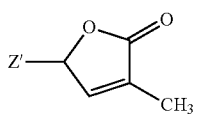

wherein Z' represents a chlorine atom or a bromine atom;

[12] A process for producing a compound represented by the formula:

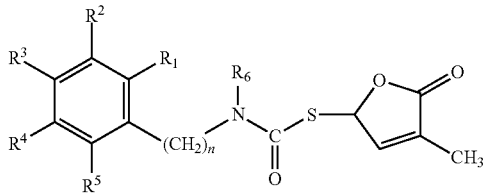

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and n represents an integer of 0, 1 or 2, which comprises reacting a compound represented by the formula:

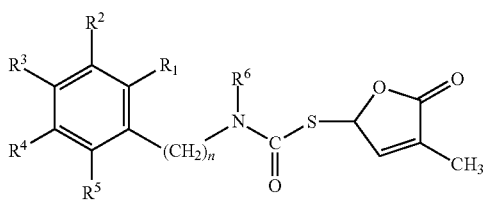

wherein $R^1$, $R^2$, $R^3$, $R^4$, $R^5$, $R^6$ and n are as defined above, with an oxidation agent;

[13] A process for producing a compound represented by the formula:

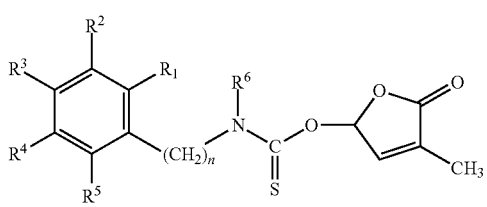

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and n represents an integer of 0, 1 or 2, which comprises reacting a compound represented by the formula:

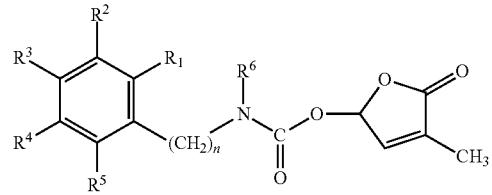

wherein $R^1$, $R^2$, $R^3$, $R^4$, $R^5$, $R^6$ and n are as defined above, with a compound represented by the formula:

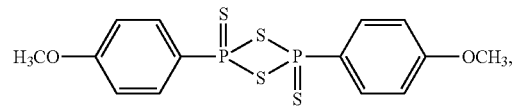

in an organic solvent;

[14] An agent for controlling a root parasitic plant comprising the compound according to any one of the above [1] to [8] as an active ingredient;

[15] A method for controlling a root parasitic plant, which comprises applying an effective amount of the compound according to any one of the above [1] to [8] to an agricultural land before sowing an agricultural crop; and

[16] Use of the compound according to any one of the above [1] to [8] as an agent for controlling a root parasitic plant.

Effect of Invention

The compound of the present invention can induce the germination of seeds of root parasitic plants in the absence of a host. In the absence of a host, root parasitic plants after the germination are killed due to lack of nutrients. Therefore, the compound of the present invention can control root parasitic plants.

DESCRIPTION OF EMBODIMENTS

Examples of the halogen atom represented by $R^1$, $R^2$, $R^3$, $R^4$ or $R^5$ include a fluorine atom, a chlorine atom, and a bromine atom.

Examples of the lower alkyl group represented by $R^1$, $R^2$, $R^3$, $R^4$ or $R^5$ include a C1-C4 alkyl group, specifically a methyl group, an ethyl group, a n-propyl group and a n-butyl group, preferably a methyl group.

Examples of the lower alkoxy group represented by $R^1$, $R^2$, $R^3$, $R^4$ or $R^5$ include a C1-C4 alkoxy group, specifically a methoxy group, an ethoxy group, a n-propoxy group, and a n-butoxy group.

When $R^1$ and $R^2$ are linked together to form a lower alkylenedioxy group, examples of the lower alkylenedioxy group include a C1-C2 alkylenedioxy group.

When $R^2$ and $R^3$ are linked together to form a lower alkylenedioxy group, examples of the lower alkylenedioxy group include a C1-C2 alkylenedioxy group.

Examples of the lower alkyl group represented by $R^6$ include a C1-C4 alkyl group, specifically a methyl group, an ethyl group, a n-propyl group, and a n-butyl group, preferably a methyl group.

The compound of the present invention includes optically-active substances due to an asymmetric carbon at the 5 position of the butenolide.

In the context of the invention, examples of the halogen atom represented by Z include a fluorine atom, a chlorine atom, and a bromine atom.

The compound of the present invention can be produced by the following production methods.

Production Method 1

Among the compound of the present invention, a compound represented by the formula (2):

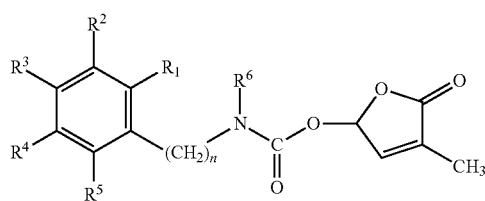

(2)

wherein $R^1$, $R^2$, $R^3$, $R^4$, $R^5$, $R^6$ and n are as defined above (compound (2)), can be produced by reacting a compound represented by the formula (3):

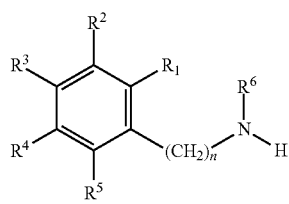

(3)

wherein $R^1$, $R^2$, $R^3$, $R^4$, $R^5$, $R^6$ and n are as defined above (compound (3)), with a compound represented by the formula (4):

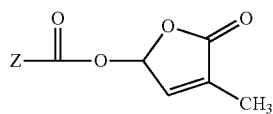

(4)

wherein Z represents a halogen atom (compound (4)), in the presence of a base.

Examples of the base to be used in the reaction include inorganic bases such as sodium hydroxide, potassium carbonate and the like, and organic bases such as triethylamine, N,N-diethylaniline, pyridine and the like.

The reaction is generally carried out in an organic solvent. Examples of the organic solvent include aromatic compounds such as benzene, toluene and the like, ether compounds such as diethyl ether, tetrahydrofuran and the like, and chlorine compounds such as dichloromethane, chloroform and the like.

The reaction temperature and the reaction time vary depending on the kind of the base or the organic solvent to be used. The reaction temperature is generally about −70 to 100° C., preferably 0 to 50° C., and the reaction time is generally about 1 to 48 hours, preferably about 5 to 24 hours.

The amount of the compound (4) to be used in the reaction is generally about 1 to 5 equivalent amounts, preferably 1 to 2 equivalent amounts, relative to the amount of the compound (3).

The amount of the base to be used in the reaction is generally about 1 to 5 equivalent amounts, preferably about 1 to 2 equivalent amounts, relative to the amount of the compound (3).

After the completion of the reaction, a posttreatment is generally carried out to obtain the target compound (2).

The compound (3) which is a starting material for production method 1 may be commercially available or synthesized by reducing the corresponding amide in a general manner. The compound (4) may be produced by hydrolyzing a compound represented by the formula (5):

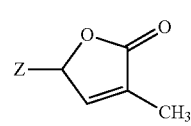

(5)

wherein Z represents a halogen atom (compound (5)), which is produced by a method described in, for example, E. M. Mungnus, B. J. Zwanenburg, Journal of Agricultural and Food Chemistry, 1992, 49, 1066-1070 to obtain a compound represented by the formula (6):

(compound (6))

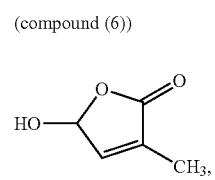

(6)

and then reacting the compound (6) with phosgene.

Production Method 2

Among the compound of the present invention, a compound represented by the formula (7):

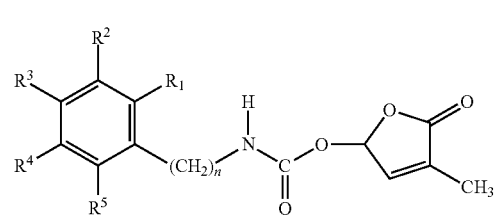

(7)

wherein $R^1$, $R^2$, $R^3$, $R^4$, $R^5$, and n are as defined above (compound (7)), can be produced by reacting a compound represented by the formula (8):

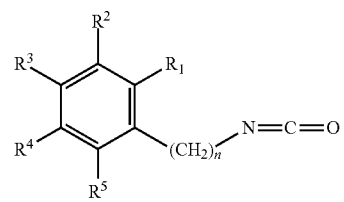

(8)

wherein $R^1$, $R^2$, $R^3$, $R^4$, $R^5$, and n are as defined above (compound (8)), with 3-methyl-5-hydroxybutenolide, i.e., a compound represented by the formula (6):

(compound (6))

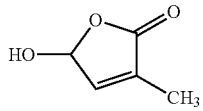

(6)

in the presence of a base.

Examples of the base to be used include organic bases such as triethylamine, N,N-diethylaniline, pyridine and the like.

The reaction is generally carried out in an organic solvent. Examples of the organic solvent include aromatic compounds such as benzene, toluene and the like, ether compounds such as diethyl ether, diisopropyl ether, tetrahydrofuran and the like, and chlorine compounds such as dichloromethane, chloroform and the like.

The reaction temperature and the reaction time vary depending on the kind of the base or the organic solvent to be used. The reaction temperature is generally about −70 to 50° C., preferably 0 to 30° C., and the reaction temperature is generally about 1 to 48 hours, preferably about 5 to 24 hours.

The amount of the compound (6) to be used in the reaction is generally about 1 to 5 equivalent amounts, preferably 1 to 2 equivalent amounts, relative to the amount of the compound (8).

The amount of the base to be used in the reaction is generally about 0.01 to 0.5 equivalent amounts, preferably about 0.05 to 0.2 equivalent amounts, relative to the amount of the compound (8).

After the completion of the reaction, a posttreatment is generally carried out to obtain the target compound (7).

The compound (8) which is a starting material for production method 2 may be commercially available or synthesized by converting the corresponding amine to the isocyanate with phosgene in a general manner.

Production Method 3

Among the compound of the present invention, a compound represented by the formula (9):

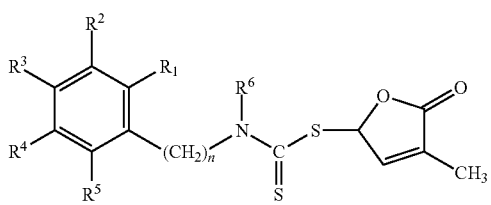

(9)

wherein $R^1$, $R^2$, $R^3$, $R^4$, $R^5$, $R^6$ and n are as defined above (compound (9)), can be produced by reacting a compound represented by the formula (10):

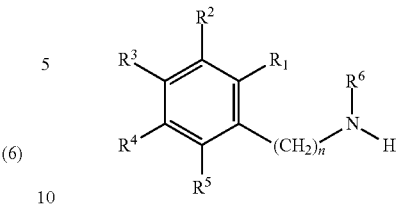

(10)

wherein $R^1$, $R^2$, $R^3$, $R^4$, $R^5$, $R^6$ and n are as defined above (compound (10)), with carbon disulfide in the presence of a base (first reaction), and then reacting the resulting product with a compound the formula (11):

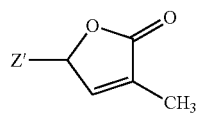

(11)

wherein Z' represents a chlorine atom or a bromine atom (compound (11)) (second reaction).

Examples of the base to be used in the first reaction include inorganic bases such as sodium hydroxide, potassium hydroxide, potassium carbonate and the like, preferably potassium hydroxide.

The first reaction is generally carried out in a solvent such as water or an organic solvent. The organic solvent to be used in the first reaction include alcohol compounds such as methanol, ethanol and the like. Particularly preferred is a mixed solvent of water and an alcohol compound.

The reaction temperature and the reaction time vary depending on the kind of the base or the solvent to be used. The reaction temperature is generally about −20 to 30° C., preferably 0 to 20° C., and the reaction time is generally about 1 to 48 hours, preferably about 5 to 24 hours.

The amount of carbon disulfide and base to be used in the first reaction is generally about 1 to 5 equivalent amounts, preferably about 1 to 2 equivalent amounts, respectively, relative to the amount of the compound (10). A dithiocarbamate obtained in the first reaction is not separated and is directly reacted with the compound (11) in the same reactor (the second reaction).

In the second reaction, the amount of the compound (11) is generally about 1 to 5 equivalent amounts, preferably about 1 to 2 equivalent amounts, relative to the amount of the compound (10).

The reaction temperature and the reaction time in the second reaction vary depending on the kind of the base or the solvent to be used in the first reaction. The reaction temperature is generally about −10 to 30° C., preferably 0 to 20° C., and the reaction time is generally about 1 to 48 hours, preferably about 5 to 24 hours.

After the completion of the reaction, a posttreatment is generally carried out to obtain the target compound (9).

Production Method 4

Among the compound of the present invention, a compound represented by the formula (12):

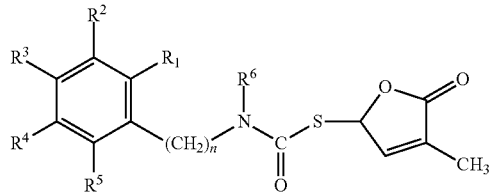

(12)

wherein $R^1$, $R^2$, $R^3$, $R^4$, $R^5$, $R^6$ and n are as defined above (compound (12)), can be produced by treating a compound represented by the formula (9):

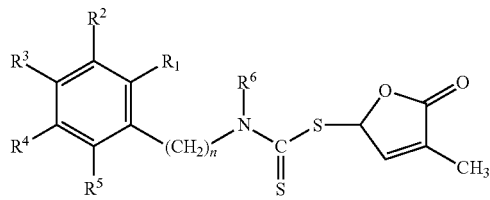

(9)

wherein $R^1$, $R^2$, $R^3$, $R^4$, $R^5$, $R^6$ and n are as defined above (compound (9)), with an oxidation agent.

Examples of the oxidation agent to be used in the reaction include organic peracids such as peracetic acid, meta-chloroperbenzoic acid and the like.

The reaction is generally carried out in an organic solvent. Examples of the organic solvent include chlorine compounds such as dichloromethane, chloroform and the like.

The reaction temperature and the reaction time vary depending on the kind of the oxidation agent or the organic solvent to be used. The reaction temperature is generally about −70 to 50° C., preferably 0 to 30° C., and the reaction time is generally about 1 to 48 hours, preferably about 5 to 24 hours.

The amount of the oxidation agent to be used in the reaction is generally about 1 to 5 equivalent amounts, preferably 1 to 2 equivalent amounts, relative to the amount of the compound (9).

After the completion of the reaction, a posttreatment is generally carried out to obtain the target compound (12).

Production Method 5

Among the compound of the present invention, a compound represented by the formula (13):

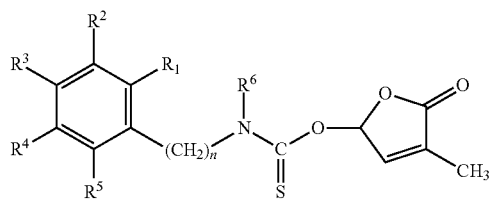

(13)

wherein $R^1$, $R^2$, $R^3$, $R^4$, $R^5$, $R^6$ and n are as defined above (compound (13)), can be produced by reacting a compound represented by the formula (2):

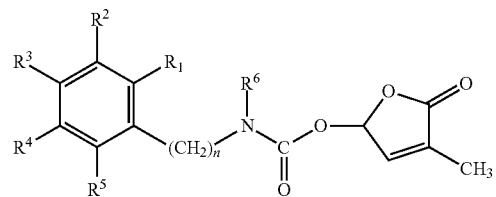

(2)

wherein $R^1$, $R^2$, $R^3$, $R^4$, $R^5$, $R^6$ and n are as defined above (compound (2)), with a compound represented by the formula (14):

(compound (14))

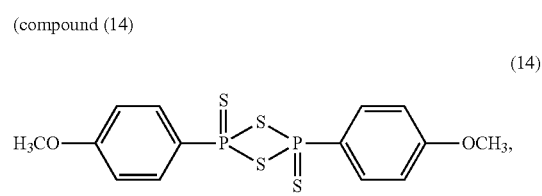

(14)

Lawesson's reagent: 2,4-bis-(4-methoxyphenyl)-1,3-dithia-2,4-diphosphetane 2,4-disulfide) in an organic solvent.

Examples of the organic solvent to be used in the reaction include aromatic compounds such as toluene, xylene and the like.

The reaction temperature and the reaction time vary depending on the kind of the organic solvent to be used. The reaction temperature is generally about 50° C. to reflux temperature, preferably 100 to 120° C., and the reaction time is generally about 10 minutes to 2 hours, preferably about 30 minutes to 1 hour.

The load amount of the compound (14) (i.e., Lawesson's reagent) to be used in the reaction is generally about 0.5 to 2 equivalent amounts, preferably about 1 to 1.5 equivalent amounts, relative to the amount of the compound (2).

After the completion of the reaction, a posttreatment is generally carried out to obtain the target compound (13).

Examples of the compound of the present invention includes the following compound: 4-methyl-5-oxo-2,5-dihydrofuran-2-yl phenylcarbamate 4-methyl-5-oxo-2,5-dihydrofuran-2-yl 2-fluorophenylcarbamate 4-methyl-5-oxo-2,5-dihydrofuran-2-yl o-tolylcarbamate 4-methyl-5-oxo-2,5-dihydrofuran-2-yl 2-ethylphenylcarbamate 4-methyl-5-oxo-2,5-dihydrofuran-2-yl 2-isopropylphenylcarbamate 4-methyl-5-oxo-2,5-dihydrofuran-2-yl 2-tert-butylphenylcarbamate 4-methyl-5-oxo-2,5-dihydrofuran-2-yl 2-methoxyphenylcarbamate 4-methyl-5-oxo-2,5-dihydrofuran-2-yl 2,3-dimethylphenylcarbamate 4-methyl-5-oxo-2,5-dihydrofuran-2-yl 4-methoxy-3-methylphenylcarbamate 4-methyl-5-oxo-2,5-dihydrofuran-2-yl 3-chloro-4-methoxyphenylcarbamate 4-methyl-5-oxo-2,5-dihydrofuran-2-yl 3,5-dichloro-4-methoxyphenylcarbamate 4-methyl-5-oxo-2,5-dihydrofuran-2-yl benzo[d][1,3]dioxol-5-ylcarbamate 4-methyl-5-oxo-2,5-dihydrofuran-2-yl benzo[d][1,3]dioxol-4-ylcarbamate 4-methyl-5-oxo-2,5-dihydrofuran-2-yl naphthalen-2-yl carbamate 4-methyl-5-oxo-2,5-dihydrofuran-2-yl naphthalen-2-ylcarbamate 4-methyl-5-oxo-2,5-dihydrofuran-2-yl methyl(phenyl)carbamate 4-methyl-5- oxo-2,5-dihydrofuran-2-yl ethyl(phenyl)carbamate 4-methyl-5-oxo-2,5-dihydrofuran-2-yl 2-chlorophenyl(methyl)carbamate 4-methyl-5-oxo-2,5-dihydrofuran-2-yl methyl(o-tolyl)carbamate 4-methyl-5-oxo-2,5-dihydrofuran-2-yl 2-methoxyphenyl(methyl)carbamate 4-methyl-5-oxo-2,5-dihydrofuran-2-yl benzylcarbamate 4-methyl-5-oxo-2,5-dihydrofuran-2-yl 2-chlorobenzylcarbamate 4-methyl-5-oxo-2,5-dihydrofuran-2-yl 2-methylbenzylcarbamate 4-methyl-5-oxo-2,5-dihydrofuran-2-yl 2-methoxybenzylcarbamate 4-methyl-5-oxo-2,5-dihydrofuran-2-yl 2-methoxyphenethylcarbamate 4-methyl-5-oxo-2,5-dihydrofuran-2-yl 2-methoxybenzyl(methyl)carbamate 4-methyl-5-oxo-2,5-dihydrofuran-2-yl 2-methoxyphenethyl(methyl)carbamate 4-methyl-5-oxo-2,5-dihydrofuran-2-yl methyl(phenyl)thiolcarbamate 4-methyl-5-oxo-2,5-dihydrofuran-2-yl methyl(phenyl)dithiocarbamate 4-methyl-5-oxo-2,5-dihydrofuran-2-yl 2-(2,3-dimethylphenyl)ethylcarbamate 4-methyl-5-oxo-2,5-dihydrofuran-2-yl 2-(3,4-dimethylphenyl)ethylcarbamate 4-methyl-5-oxo-2,5-dihydrofuran-2-yl 2-(3,4-methylenedioxyphenyl)ethylcarbamate 4-methyl-5-oxo-2,5-dihydrofuran-2-yl phenethylcarbamate 4-methyl-5-oxo-2,5-dihydrofuran-2-yl benzyl(methyl)carbamate.

Among the compound of the present invention, preferred are 4-methyl-5-oxo-2,5-dihydrofuran-2-yl benzylcarbamate, 4-methyl-5-oxo-2,5-dihydrofuran-2-yl phenethylcarbamate, 4-methyl-5-oxo-2,5-dihydrofuran-2-yl methyl(phenyl)carbamate, and 4-methyl-5-oxo-2,5-dihydrofuran-2-yl benzyl(methyl)carbamate.

The compound of the present invention is generally diluted with a mixed solvent of water and an organic solvent such as alcohols (e.g., methanol and ethanol) and ketones (e.g., acetone and methyl ethyl ketone), and applied to seeds of root parasitic plants, or agricultural lands containing seeds of root parasitic plants, before sowing agricultural crops.

By the application of the compound of the present invention, it is possible to germinate seeds of root parasitic plants in the absence of nutrient sources and thus to kill the root parasitic plants, i.e., control the root parasitic plants. Therefore, it is possible to control the inhibition of the growth of agricultural crops by root parasitic plants.

Examples of the agricultural lands include those in which leguminous plants, sorghum, or corns are grown.

Examples of the root parasitic plants to be controlled by the compound of the present invention include those belonging to the genus *Striga*, the genus *Orobanche*, and the genus *Alectra*.

EXAMPLES

Hereinafter, the present invention is described specifically by way of production examples and test examples to which the present invention is not limited.

Production Example 1

Synthesis of 4-methyl-5-oxo-2,5-dihydrofuran-2-yl phenylcarbamate (Compound No. 1)

In diisopropyl ether (10 ml), 3-methyl-5-hydroxybutenolide (0.800 g, 7.01 mmol) was stirred, and thereto was added with stirring triethylamine (5 to 6 drops), followed by phenyl isocyanate (0.700 g, 5.85 mmol). Then, the mixture was stirred overnight. After the completion of the reaction, the reaction solution was quenched with 1M hydrochloric acid, extracted with diethyl ether, and washed with saturated sodium chloride solution. The resulting organic layer was dried over magnesium sulfate, purified by a column chromatography to give the target compound (0.05 g).

Crystalline solid, m.p 112-115° C.
$^1$H NMR (CDCl$_3$): δ=2.00-2.01 (m, 3H), 6.92-6.96 (s, 1H), 7.25-7.36 (m, 6H)

Production Example 2

Synthesis of 4-methyl-5-oxo-2,5-dihydrofuran-2-yl benzylcarbamate (Compound No. 2)

Into diisopropyl ether (10 ml) was dissolved 3-methyl-5-hydroxybutenolide (1.14 g, 10.0 mmol), and thereto were added triethylamine (3 drops) and benzyl isocyanate (1.33 g, 10.0 mmol). Then, the mixture was stirred at room temperature overnight. After the completion of the reaction, the reaction solution was quenched with saturated ammonium chloride solution, extracted with ethyl acetate, and washed with saturated sodium chloride solution. The resulting organic layer was dried over magnesium sulfate, and purified by a column chromatography to give the target compound (0.98 g).

Crystalline solid, m.p 72-75° C.
$^1$H NMR (CDCl$_3$): δ=1.93-1.97 (m, 3H), 4.40-4.42 (m, 2H), 5.23 (br s, 1H), 6.86-6.90 (m, 1H), 7.26-7.38 (m, 6H)

Production Example 3

Synthesis of 4-methyl-5-oxo-2,5-dihydrofuran-2-yl phenethylcarbamate (Compound No. 3)

In diisopropyl ether (5 ml) was dissolved 3-methyl-5-hydroxybutenolide (0.44 g, 3.83 mmol), and thereto were added triethylamine (3 drops) and phenethylisocyanate (0.56 g, 3.83 mmol). Then, the mixture was stirred at room temperature overnight. After the completion of the reaction, the reaction solution was quenched with saturated ammonium chloride solution, extracted with ethyl acetate, and washed with saturated sodium chloride solution. The resulting organic layer was dried over magnesium sulfate, and purified by a column chromatography to give the target compound (0.34 g).

Crystalline solid, m.p 64-66° C.
$^1$H NMR(CDCl$_3$): δ=1.92 (s, 3H), 2.82-2.87 (m, 2H), 3.42-3.56 (m, 2H), 4.85 (br s, 1H), 6.83-6.87 (m, 1H), 7.18-7.34 (m, 6H)

Production Example 4

Synthesis of 4-methyl-5-oxo-2,5-dihydrofuran-2-yl methyl(phenyl)carbamate (Compound No. 4)

In dry dichloromethane (5 ml), 3-methyl-5-hydroxybutenolide (0.52 g, 4.53 mmol) was stirred, and thereto was added N,N-diethylaniline (0.68 g, 4.53 mmol). Then, the mixture was stirred for 10 minutes. Thereto was added triphosgene (0.450 g, 1.51 mmol), and the mixture was stirred for 2 hours. To this reaction solution was added N-methylaniline (0.430 g, 4.05 mmol), and then the mixture was reacted with stirring overnight. After the completion of the reaction, the reaction solution was quenched with 1M hydrochloric acid, washed with water, extracted with dimethyl ether, and then washed with saturated sodium chloride solution. The resulting organic layer was dried over magnesium sulfate, and purified by a column chromatography to give the target compound (0.23 g).

Crystalline solid, m.p 69-71° C.

$^1$H NMR (CDCl$_3$): δ=1.93 (s, 3H), 3.32 (s, 3H), 6.92 (s, 1H), 7.22-7.38 (m, 6H)

Production Example 5

Synthesis of 4-methyl-5-oxo-2,5-dihydrofuran-2-yl benzyl(methyl)carbamate (Compound No. 5)

Under argon atmosphere, 3-methyl-5-hydroxybutenolide (0.52 g, 4.53 mmol) was dissolved in dichloromethane (5 ml), and thereto was added N,N-diethylaniline (0.73 ml, 4.53 mmol), followed by triphosgene (0.45 g, 1.51 mmol). Then, the mixture was reacted for 2.5 hours. To the reaction solution was added N-benzylmethylamine (0.58 ml, 4.53 mmol), and the mixture was stirred for 2 days. After the completion of the reaction, the reaction solution was quenched with 1M hydrochloric acid, extracted with ethyl acetate, and washed with saturated sodium chloride solution. The resulting organic layer was dried over magnesium sulfate, and purified by a column chromatography to give the target compound (0.29 g).
Oily Substance
$^1$H NMR (CDCl$_3$): δ=1.95-1.99 (m, 3H), 2.83 (s, 3H), 4.39-4.56 (m, 2H), 6.88-6.96 (m, 1H), 7.17-7.45 (m, 6H)

Production Example 6

Synthesis of 4-methyl-5-oxo-2,5-dihydrofuran-2-yl 2-phenethyl(methyl)carbamate (Compound No. 6)

Under argon atmosphere, 3-methyl-5-hydroxybutenolide (0.52 g, 4.53 mmol) was dissolved in dichloromethane (5 ml), and thereto was added N,N-diethylaniline (0.73 ml, 4.53 mmol), followed by triphosgene (0.45 g, 1.51 mmol). Then, the mixture was reacted for 2.5 hours. To the reaction solution was added N-(2-phenethyl)methylamine (0.62 ml, 4.53 mmol), and then the mixture was stirred for 2 days. After the completion of the reaction, the reaction solution was quenched with 1M hydrochloric acid, extracted with ethyl acetate, and washed with saturated sodium chloride solution. The resulting organic layer was dried over magnesium sulfate, and purified by a column chromatography to give the target compound (0.20 g).
Oily Substance
$^1$H NMR (CDCl$_3$): δ=1.95-1.99 (m, 3H), 2.90-3.00 (m, 2H), 3.03 (s, 3H), 3.60-3.75 (m, 2H), 7.17-7.45 (m, 6H), 7.52 (s, 1H)

Production Example 7

Synthesis of 4-methyl-5-oxo-2,5-dihydrofuran-2-yl methyl(phenyl)dithiocarbamate (Compound No. 7)

To an aqueous solution of 20% potassium hydroxide (1.50 g) was added N-methylaniline (0.480 g, 4.53 mmol), and the mixture was stirred. Thereto was added dropwise carbon disulfide (0.340 g, 4.53 mmol), and the mixture was stirred with ice-cooling for 2.5 hours. Thereto was added a solution of 5-bromo-3-methyl-butenolide (0.790 g, 4.53 mmol) in toluene, and then the mixture was reacted with stirring overnight. After the completion of the reaction, the reaction solution was quenched with saturated aqueous solution of ammonium chloride, extracted with ethyl acetate, and washed with saturated sodium chloride solution. The resulting organic layer was dried over magnesium sulfate, and then purified by a column chromatography to give the target compound (0.69 g).

Crystalline solid, m.p 108-110° C.
$^1$H NMR (CDCl$_3$): δ=1.88-1.89 (m, 3H), 3.79 (s, 3H), 7.03-7.04 (m, 1H), 7.09-7.50 (m, 6H)

Production Example 8

Synthesis of 4-methyl-5-oxo-2,5-dihydrofuran-2-yl methyl(phenyl)thiolcarbamate (Compound No. 8)

In methylene chloride (3 ml), 4-methyl-5-oxo-2,5-dihydrofuran-2-yl methyl(phenyl)dithiocarbamate (0.360 g, 1.29 mmol) was stirred. Thereto was added meta-chloroperbenzoic acid (0.222 g, 1.28 mmol), and the mixture was stirred while ice-cooling to react for 2.5 hours. After the completion of the reaction, the reaction solution was quenched with an aqueous solution of sodium thiosulfate, extracted with methylene chloride, and washed with saturated sodium chloride solution. The resulting organic layer was dried over magnesium sulfate, and then purified by a column chromatography to give the target compound (0.03 g).
Crystalline solid, m.p 110° C.
$^1$H NMR(CDCl$_3$): δ=1.88-1.89 (m, 3H), 3.37-3.39 (m, 3H), 6.67-6.69 (m, 1H), 6.94-6.95 (m, 1H), 7.26-7.46 (m, 5H)

Production Example 9

Synthesis of 4-methyl-5-oxo-2,5-dihydrofuran-2-yl 2-(2,3-dimethylphenyl)ethylcarbamate (Compound No. 9)

Under argon atmosphere, 5-hydroxy-3-methylbutenolide (0.29 g, 2.55 mmol) was dissolved in dichloromethane (3.5 ml), and thereto was added N,N-diethylaniline (0.55 ml, 3.4 mmol), followed by triphosgene (0.30 g, 1.0 mmol). Then, the mixture was reacted for 2 hours. To the reaction mixture was added 2-(2,3-dimethylphenyl)ethylamine (0.38 g, 2.55 mmol), and then the mixture was stirred overnight. The reaction solution was quenched with 1M hydrochloric acid, and then extracted with dichloromethane. The resulting organic layer was washed with saturated sodium chloride solution, dried over potassium carbonate, concentrated, and then purified by a column chromatography to give the target compound (0.10 g, yield 14%).
White solid, m. p. 100-102° C.
$^1$H-NMR (300 MHz, CDCl$_3$) δ 1.96-1.97 (br s, 3H), 2.23 (s, 3H), 2.29 (s, 3H), 2.89 (t, J=6.9 Hz, 2H), 3.37-3.49 (m, 2H), 4.86 (br s, 1H), 6.83-7.06 (m, 5H)

Production Example 10

Synthesis of 4-methyl-5-oxo-2,5-dihydrofuran-2-yl 2-(3,4-dimethylphenyl)ethylcarbamate (Compound No. 10)

Under argon atmosphere, 5-hydroxy-3-methylbutenolide (0.06 g, 0.53 mmol) was dissolved in dichloromethane (1 ml), and thereto was added N,N-diethylaniline (0.10 ml, 0.62 mmol), followed by triphosgene (0.05 g, 1.8 mmol). Then, the mixture was reacted for 2 hours. To the reaction mixture was added 2-(3,4-dimethylphenyl)ethylamine (0.08 g, 0.53 mmol), and then the mixture was stirred overnight. The reaction solution was quenched with 1M hydrochloric acid, and then extracted with dichloromethane. The resulting organic layer was washed with saturated sodium chloride solution, dried over anhydrous magnesium sulfate, concentrated, and then purified by a column chromatography to give the target compound (0.011 g, yield 70).

White solid, m. p. 103-105° C.

$^1$H-NMR (300 MHz, CDCl$_3$) δ 1.96 (br s, 3H), 2.23 (s, 3H), 2.24 (s, 3H), 2.77 (t, J=6.9 Hz, 2H), 3.43-3.51 (m, 2H), 4.82 (br s, 1H), 6.84-7.08 (m, 5H)

Production Example 11

Synthesis of 4-methyl-5-oxo-2,5-dihydrofuran-2-yl 2-(3,4-methylenedioxyphenyl)ethylcarbamate (Compound No. 11)

Under argon atmosphere, 5-hydroxy-3-methylbutenolide (0.10 g, 0.876 mmol) was dissolved in diisopropyl ether (5 m), and thereto was added triethylamine (0.13 ml, 0.94 mmol), followed by 2-(3,4-methylenedioxyphenyl)ethylisocyanate (0.167 g, 0.876 mmol). Then, the mixture was stirred overnight. The reaction solution was quenched with 1M hydrochloric acid, and then extracted with ethyl acetate. The resulting organic layer was washed with saturated sodium chloride solution, dried over anhydrous magnesium sulfate, concentrated, and then purified by a column chromatography to give the target compound (0.182 g, yield 68%).

White solid, m. p. 127-129° C.

$^1$H-NMR (300 MHz, CDCl$_3$) δ 1.97 (br s, 3H), 2.76 (t, J=6.9 Hz, 2H), 3.40-3.48 (m, 2H), 4.82 (br s, 1H), 5.94 (s, 2H), 6.81-6.87 (m, 5H)

Test Example 1

Test for Germination Stimulation Activity on *Striga*

First, 10 μmol of each test compound was weighed and dissolved in 2 ml of acetone. Each solution was diluted with distilled water to obtain a 10 μM solution. Next, a bottom of a petri dish was covered with a filter paper, and conditioned seeds of *Striga* (*Striga hermonthica*) were placed on the filter paper, and then 20 μl of each diluted solution of test compound was applied to the seeds. For maintaining the humidity, a wet filter paper was prepared as long as water droplets were not dripped from the filter paper, and folded into four, and then placed onto the center of the petri dish. The petri dish was sealed with Parafilm®, and then covered with aluminum foil, and then incubated at 30° C. Twenty four (24) hours later, the number of germinated seeds was counted, and then a germination rate (%) was calculated by using the following formula:

Germination rate(%)=(the number of germinated seeds/the total number of seeds)×100

The test compounds and the germination rates are shown in Tables 1 and 2. When no test compound was used in this test, the germination rate was 0%.

TABLE 1

| Compound No. | Structure | Germination rate (%) |
|---|---|---|
| 1 | | 2.6 |
| 2 | 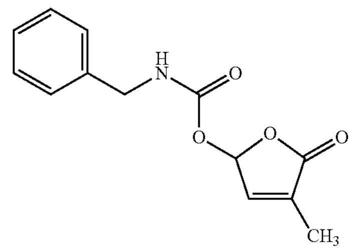 [SMILES: CC1=CC(OC(=O)NCc2ccccc2)OC1=O] | 38.1 |
| 3 | 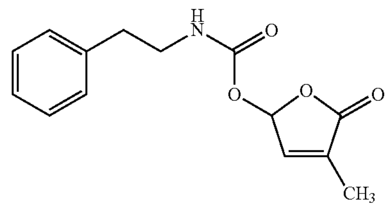 [SMILES: CC1=CC(OC(=O)NCCc2ccccc2)OC1=O] | 54.0 |
| 4 | 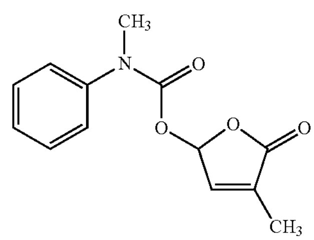 [SMILES: CC1=CC(OC(=O)N(C)c2ccccc2)OC1=O] | 53.5 |
| 5 | 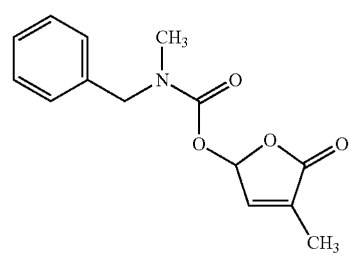 [SMILES: CC1=CC(OC(=O)N(C)Cc2ccccc2)OC1=O] | 48.4 |
| 6 | 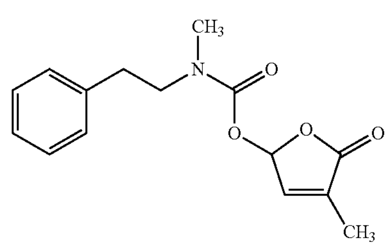 [SMILES: CC1=CC(OC(=O)N(C)CCc2ccccc2)OC1=O] | 28.0 |

TABLE 2

| Compound No. | Structure | Germination rate (%) |
|---|---|---|
| 7 | [structure] | 32.6 |
| 8 | [structure] | 12.0 |
| 9 | [structure] | 32.0 |
| 10 | [structure] | 43.0 |
| 11 | [structure] | 37.0 |

Test Example 2

Test for Germination Stimulation Activity on *Orobanche*

First, 10 μmol of each test compound was weighed and dissolved in 2 ml of acetone. Each solution was diluted with distilled water to obtain a 10 μM solution. Next, a bottom of a petri dish was covered with a filter paper, and conditioned seeds of *Orobanche* (*Orobanche minor*) were placed on the filter paper, and then 20 μl of each diluted solution of test compound was applied to the seeds. For maintaining the humidity, a wet filter paper was prepared as long as water droplets were not dripped from the filter paper, and folded into four, and then placed onto the center of the petri dish. The petri dish was sealed with Parafilm®, and then covered with aluminum foil, and then incubated at 30° C. Four (4) days after, the number of germinated seeds was counted, and then a germination rate (%) was calculated by using the following formula:

Germination rate(%)=(the number of germinated seeds/the total number of seeds)×100

The test compounds and the germination rates are shown in Tables 3 and 4. When no test compound was used in this test, the germination rate was 0%.

TABLE 3

| Compound No. | Structure | Germination rate (%) |
|---|---|---|
| 1 | [structure] | 38.8 |

TABLE 3-continued

| Compound No. | Structure | Germination rate (%) |
|---|---|---|
| 2 | (benzyl-NH-C(=O)-O-furanone-CH3) | 61.1 |
| 3 | (phenethyl-NH-C(=O)-O-furanone-CH3) | 66.9 |
| 4 | (phenyl-N(CH3)-C(=O)-O-furanone-CH3) | 66.3 |
| 5 | (benzyl-N(CH3)-C(=O)-O-furanone-CH3) | 75.2 |
| 6 | (phenethyl-N(CH3)-C(=O)-O-furanone-CH3) | 30.4 |

TABLE 4

| Compound No. | Structure | Germination rate (%) |
|---|---|---|
| 7 | (phenyl-N(CH3)-C(=S)-S-furanone-CH3) | 15.3 |
| 8 | (phenyl-N(CH3)-C(=O)-S-furanone-CH3) | 5.4 |
| 9 | (2,3-dimethylphenethyl-NH-C(=O)-O-furanone-CH3) | 54.0 |

TABLE 4-continued

| Compound No. | Structure | Germination rate (%) |
|---|---|---|
| 10 | 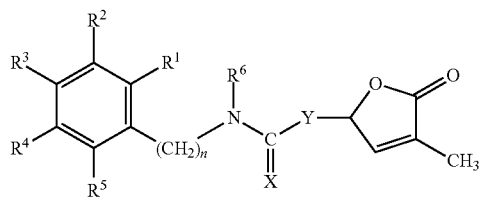 | 48.0 |
| 11 | 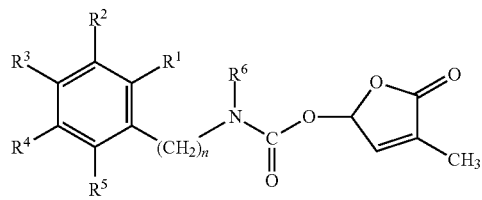 | 47.0 |

The invention claimed is:

1. A compound represented by the formula:

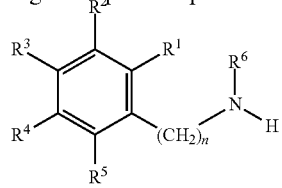

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, X and Y are the same or different and each represents an oxygen atom and a sulfur atom, and n represents an integer of 0, 1 or 2.

2. The compound according to claim 1, wherein $R^1$, $R^2$, $R^3$, $R^4$, and $R^5$ are the same or different and each represents a hydrogen atom or a lower alkyl group, or $R^2$ and $R^3$ are linked together to form a lower alkylenedioxy group.

3. The compound according to claim 1, wherein $R^1$ is a hydrogen atom or a lower alkyl group, $R^2$ is a hydrogen atom or a lower alkyl group, $R^3$ is a hydrogen atom or a lower alkyl group, or $R^2$ and $R^3$ are linked together to form a lower alkylenedioxy group, $R^4$ is a hydrogen atom, and $R^5$ is a hydrogen atom.

4. The compound according to claim 2, wherein $R^1$, $R^2$, $R^3$, $R^4$, and $R^5$ are the same or different and each represents a hydrogen atom or a methyl group, or $R^2$ and $R^3$ are linked together to form a methylenedioxy group, and $R^6$ is a hydrogen atom or a methyl group.

5. The compound according to claim 1, wherein $R^1$, $R^2$, $R^3$, $R^4$, and $R^5$ are a hydrogen atom.

6. The compound according to claim 5, wherein $R^6$ is a hydrogen atom or a methyl group.

7. The compound according to claim 1, wherein X and Y are oxygen atoms.

8. The compound according to claim 1, which is 4-methyl-5-oxo-2,5-dihydrofuran-2-yl benzylcarbamate, 4-methyl-5-oxo-2,5-dihydrofuran-2-yl phenethylcarbamate, 4-methyl-5-oxo-2,5-dihydrofuran-2-yl methyl(phenyl)carbamate, or 4-methyl-5-oxo-2,5-dihydrofuran-2-yl benzyl(methyl)carbamate.

9. A process for producing a compound represented by the formula:

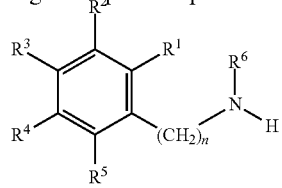

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and n represents an integer of 0, 1 or 2, which comprises reacting a compound represented by the formula:

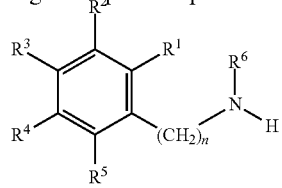

wherein $R^1$, $R^2$, $R^3$, $R^4$, $R^5$, $R^6$ and n are as defined above, with a compound represented by the formula:

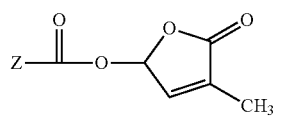

wherein Z represents a halogen atom, in the presence of a base.

10. A process for producing a compound represented by the formula:

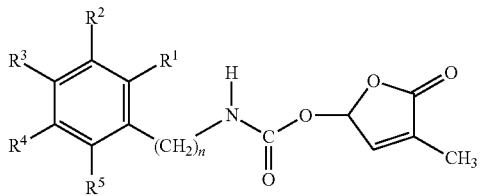

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, and n represents an integer of 0, 1 or 2, which comprises reacting a compound represented by the formula:

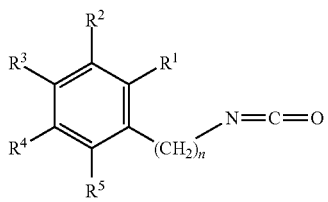

wherein $R^1$, $R^2$, $R^3$, $R^4$, $R^5$ and n are as defined above, with a compound represented by the formula:

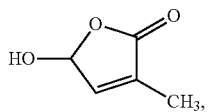

in the presence of a base.

11. A process for producing a compound represented by the formula:

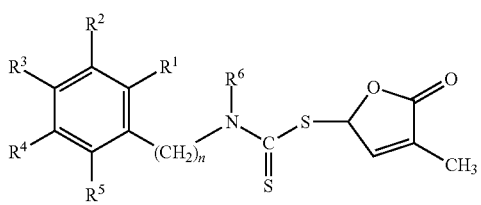

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and n represents an integer of 0, 1 or 2, which comprises reacting a compound represented by the formula:

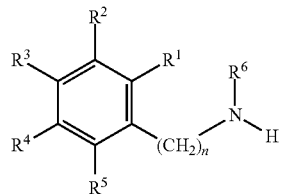

wherein $R^1$, $R^2$, $R^3$, $R^4$, $R^5$, $R^6$ and n are as defined above, with carbon disulfide in the presence of a base, and then reacting the resulting compound with a compound represented by the formula:

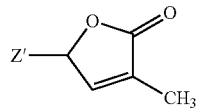

wherein Z' represents a chlorine atom or a bromine atom.

12. A process for producing a compound represented by the formula:

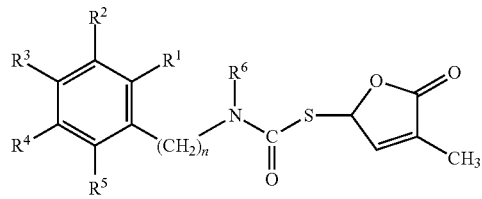

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and n represents an integer of 0, 1 or 2, which comprises reacting a compound represented by the formula:

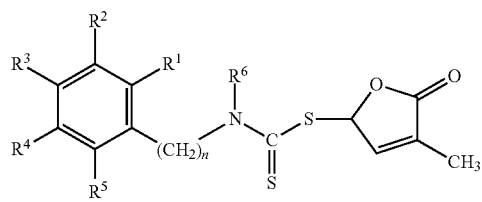

wherein $R^1$, $R^2$, $R^3$, $R^4$, $R^5$, $R^6$ and n are as defined above, with an oxidation agent.

13. A process for producing a compound represented by the formula:

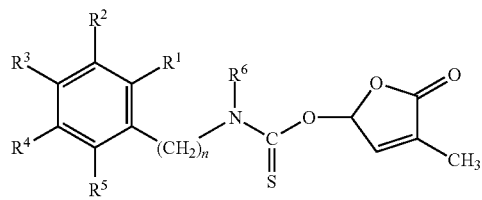

wherein $R^1$, $R^2$, $R^3$, $R^4$, and $R^5$ are the same or different and each represents a hydrogen atom, a halogen atom, a lower alkyl group, or a lower alkoxy group, or $R^1$ and $R^2$ are linked together to form a lower alkylenedioxy group, or $R^1$ and $R^2$ together with the adjacent carbon atoms form a benzene ring, or $R^2$ and $R^3$ are linked together to form a lower alkylenedioxy group, or $R^2$ and $R^3$ together with the adjacent carbon atoms form a benzene ring, $R^6$ represents a hydrogen atom or a lower alkyl group, and n represents an integer of 0, 1 or 2, which comprises reacting a compound represented by the formula:

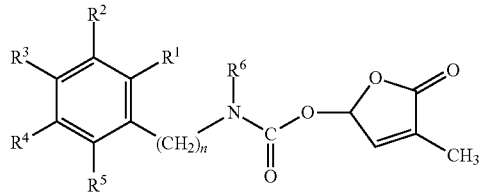

wherein $R^1$, $R^2$, $R^3$, $R^4$, $R^5$, $R^6$ and n are as defined above, with a compound represented by the formula:

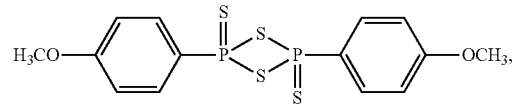

in an organic solvent.

14. A method for controlling a root parasitic plant, which comprises applying an effective amount of the compound according to claim 1 to an agricultural land before seeding an agricultural crop.

* * * * *